United States Patent
Eichhorn et al.

(10) Patent No.: US 9,851,268 B2
(45) Date of Patent: Dec. 26, 2017

(54) FLEXIBLE ELECTRICALLY CONDUCTIVE NANOTUBE SENSOR FOR ELASTOMERIC DEVICES

(71) Applicant: 7-Sigma Incorporated, Minneapolis, MN (US)

(72) Inventors: Wade R. Eichhorn, Minneapolis, MN (US); Richard M. Duda, Stillwater, MN (US); Kristian G. Wyrobek, St. Louis Park, MN (US); Ahmet Serdar Sezen, Saint Anthony, MN (US)

(73) Assignee: 7-SIGMA, Inc., Minneapolis, MN (US)

( * ) Notice: Subject to any disclaimer, the term of this patent is extended or adjusted under 35 U.S.C. 154(b) by 303 days.

(21) Appl. No.: 14/263,872

(22) Filed: Apr. 28, 2014

(65) Prior Publication Data

US 2014/0305226 A1    Oct. 16, 2014

Related U.S. Application Data

(63) Continuation of application No. 13/599,935, filed on Aug. 30, 2012, now Pat. No. 8,746,075, which is a
(Continued)

(51) Int. Cl.
*G01L 1/18* (2006.01)
*H01L 31/00* (2006.01)
(Continued)

(52) U.S. Cl.
CPC .......... *G01L 1/2206* (2013.01); *A61B 5/6853* (2013.01); *G01L 9/0035* (2013.01);
(Continued)

(58) Field of Classification Search
CPC .................................. G01L 1/18; H01L 31/00
(Continued)

(56) References Cited

U.S. PATENT DOCUMENTS

| 3,739,644 A | 6/1973 | Underwood |
| 3,791,205 A | 2/1974 | Hooker |

(Continued)

FOREIGN PATENT DOCUMENTS

| WO | WO9220096 | 11/1992 |
| WO | WO2010131820 A1 | 11/2010 |

(Continued)

OTHER PUBLICATIONS www.mech.northwestern.edu/FOM/LiuCh06v3_072505.pdf : printed on May 7, 2012.
(Continued)

*Primary Examiner* — Lisa Caputo
*Assistant Examiner* — Jamel Williams
(74) *Attorney, Agent, or Firm* — Patterson Thuente Pedersen, P.A.

(57) ABSTRACT

A flexible substrate has a major surface and a sensor attached to and aligned with the major surface of the substrate. The sensor may have an elastic body containing conductive nanotubes homogeneously distributed therein to form a conductive path and at least two electrodes in electrical connection with the conductive path. Balloons and flexible elements used in medical procedures are particularly useful.

21 Claims, 8 Drawing Sheets

Related U.S. Application Data continuation-in-part of application No. 13/397,737, filed on Feb. 16, 2012, now Pat. No. 8,850,897.

(51) Int. Cl.
  *G01L 1/22* (2006.01)
  *G01L 9/00* (2006.01)
  *B82Y 15/00* (2011.01)
  *A61B 5/00* (2006.01)

(52) U.S. Cl.
  CPC ..... *A61B 5/6843* (2013.01); *A61B 2562/0261* (2013.01); *A61B 2562/0285* (2013.01); *B82Y 15/00* (2013.01)

(58) Field of Classification Search
  USPC .......................................................... 73/777
  See application file for complete search history.

(56) References Cited

U.S. PATENT DOCUMENTS

| | | |
|---|---|---|
| 3,817,107 A | 6/1974 | Shimada |
| 4,362,150 A | 12/1982 | Lombardi, Jr. et al. |
| 4,411,655 A | 10/1983 | Schreck |
| 4,799,495 A | 1/1989 | Hawkins |
| 4,921,479 A | 5/1990 | Grayzel |
| 5,335,549 A | 8/1994 | Kato |
| 5,483,994 A | 1/1996 | Maurer |
| 5,817,061 A | 10/1998 | Goodwin et al. |
| 5,823,992 A | 10/1998 | Salmon et al. |
| 6,183,443 B1 | 2/2001 | Kratoska et al. |
| 6,814,715 B2 | 11/2004 | Bonutti et al. |
| 7,081,030 B2 | 7/2006 | Liu et al. |
| 7,129,467 B2 * | 10/2006 | Wincheski ............. B82Y 10/00 250/214.1 |
| 7,278,324 B2 | 10/2007 | Smits et al. |
| 7,399,400 B2 | 7/2008 | Soundarrajan et al. |
| 7,404,338 B2 | 7/2008 | Hierold et al. |
| 7,453,085 B2 | 11/2008 | Chang et al. |
| 7,598,723 B2 | 10/2009 | Gaillard et al. |
| 7,645,497 B2 | 1/2010 | Spath et al. |
| 7,673,521 B2 | 3/2010 | Ajayan |
| 7,699,864 B2 | 4/2010 | Kick et al. |
| 7,730,547 B2 | 6/2010 | Barrera |
| 7,766,876 B2 | 8/2010 | Hanagasaki |
| 7,828,774 B2 | 11/2010 | Harding et al. |
| 7,927,309 B2 | 4/2011 | Palm |
| 8,021,338 B2 | 9/2011 | Adams |
| 8,075,529 B2 | 12/2011 | Nakajima |
| 8,119,758 B2 | 2/2012 | Sakurai et al. |
| 8,132,468 B2 | 3/2012 | Radivojevic |
| 8,250,927 B2 | 8/2012 | Anand et al. |
| 8,251,955 B2 | 8/2012 | Mittermeyer et al. |
| 8,282,648 B2 | 10/2012 | Tekulve |
| 8,308,690 B2 | 11/2012 | Forrest |
| 8,313,443 B2 | 11/2012 | Tom |
| 8,492,755 B2 | 7/2013 | Hu et al. |
| 8,495,917 B2 | 7/2013 | Radivojevic |
| 8,587,422 B2 | 11/2013 | Andrews et al. |
| 8,591,466 B2 | 11/2013 | Wenchell et al. |
| 8,746,075 B2 * | 6/2014 | Eichhorn ............. G01L 9/0035 73/777 |
| 8,820,173 B2 | 9/2014 | Clark et al. |
| 8,840,566 B2 | 9/2014 | Seibel et al. |
| 8,850,897 B2 | 10/2014 | Eichhorn et al. |
| 8,864,745 B2 | 10/2014 | Ciavarella et al. |
| 8,943,897 B2 * | 2/2015 | Beauvais ............. A61B 5/1038 73/774 |
| 2001/0036790 A1 | 11/2001 | Kornbluh et al. |
| 2003/0032892 A1 | 2/2003 | Erlach et al. |
| 2004/0126746 A1 | 7/2004 | Toly |
| 2006/0046235 A1 | 3/2006 | Alexander et al. |
| 2006/0063973 A1 | 3/2006 | Makower |
| 2006/0115640 A1 | 6/2006 | Yodh et al. |
| 2006/0122954 A1 | 6/2006 | Podlasek et al. |
| 2007/0010702 A1 | 1/2007 | Wang et al. |
| 2007/0129719 A1 | 6/2007 | Kendale et al. |
| 2007/0132043 A1 | 6/2007 | Bradley et al. |
| 2007/0191766 A1 * | 8/2007 | McMorrow ........... A61M 25/10 604/103.01 |
| 2007/0205701 A1 | 9/2007 | Grumm |
| 2007/0239108 A1 | 10/2007 | Albrecht et al. |
| 2008/0033569 A1 | 2/2008 | Ferren et al. |
| 2008/0129278 A1 | 6/2008 | Dai et al. |
| 2008/0145616 A1 | 6/2008 | Gharib et al. |
| 2008/0154373 A1 | 6/2008 | Protopsaltis et al. |
| 2008/0172033 A1 | 7/2008 | Keith et al. |
| 2008/0238882 A1 * | 10/2008 | Sivarajan ................ G06F 3/045 345/174 |
| 2008/0294184 A1 | 11/2008 | Smith |
| 2009/0016780 A1 | 1/2009 | Souma et al. |
| 2009/0024140 A1 | 1/2009 | Allen et al. |
| 2009/0036744 A1 | 2/2009 | Vayser |
| 2009/0171271 A1 | 7/2009 | Webster et al. |
| 2009/0198117 A1 | 8/2009 | Cooper et al. |
| 2009/0208915 A1 | 8/2009 | Pugh |
| 2009/0216196 A1 | 8/2009 | Drontle et al. |
| 2009/0254288 A1 | 10/2009 | Chase et al. |
| 2009/0293631 A1 | 12/2009 | Radivojevic |
| 2009/0308742 A1 | 12/2009 | Paranjape |
| 2009/0309172 A1 | 12/2009 | Liu et al. |
| 2010/0003657 A1 | 1/2010 | Shibui et al. |
| 2010/0154556 A1 | 6/2010 | Yin |
| 2010/0191296 A1 | 7/2010 | Lyon |
| 2010/0228157 A1 | 9/2010 | Tom |
| 2010/0294976 A1 | 11/2010 | Ajayan et al. |
| 2011/0089051 A1 | 4/2011 | Wang et al. |
| 2011/0148815 A1 | 6/2011 | Tsai |
| 2011/0230788 A1 | 9/2011 | Anand et al. |
| 2011/0239731 A1 | 10/2011 | Lisseman et al. |
| 2011/0275502 A1 | 11/2011 | Eichhorn |
| 2011/0306824 A1 | 12/2011 | Perron |
| 2011/0316522 A1 | 12/2011 | Shinobu |
| 2011/0319755 A1 | 12/2011 | Stein |
| 2012/0021164 A1 | 1/2012 | Sansom et al. |
| 2012/0034587 A1 | 2/2012 | Toly |
| 2012/0035437 A1 | 2/2012 | Ferren et al. |
| 2012/0073388 A1 | 3/2012 | Chibante et al. |
| 2012/0143341 A1 | 6/2012 | Zipnick |
| 2012/0207525 A1 | 8/2012 | Kim et al. |
| 2012/0226130 A1 | 9/2012 | De Graff et al. |
| 2012/0266685 A1 | 10/2012 | Choi et al. |
| 2013/0023990 A1 | 1/2013 | Zipnick et al. |
| 2013/0031987 A1 | 2/2013 | Beauvais et al. |
| 2013/0104665 A1 | 5/2013 | Biris et al. |
| 2013/0111971 A1 | 5/2013 | Pudas |
| 2013/0177888 A1 | 7/2013 | Daullary |
| 2013/0213140 A1 | 8/2013 | Eichhorn et al. |
| 2013/0218050 A1 | 8/2013 | Eichhorn et al. |
| 2013/0274663 A1 | 10/2013 | Heppe |
| 2013/0320273 A1 | 12/2013 | Kotov et al. |
| 2014/0128687 A1 | 5/2014 | White et al. |
| 2014/0142542 A1 | 5/2014 | Rosenbaum et al. |
| 2014/0150573 A1 | 6/2014 | Cannard et al. |
| 2014/0163323 A1 | 6/2014 | Mohajer-Shojaee |
| 2014/0220422 A1 | 8/2014 | Rogers et al. |
| 2014/0272870 A1 | 9/2014 | Eichhorn et al. |
| 2014/0275795 A1 | 9/2014 | Little et al. |
| 2014/0277204 A1 | 9/2014 | Sandhu |
| 2014/0349266 A1 | 11/2014 | Choi |
| 2015/0011843 A1 | 1/2015 | Toth et al. |
| 2015/0044656 A1 | 2/2015 | Eichhorn et al. |
| 2015/0064675 A1 | 3/2015 | Eichhorn et al. |
| 2015/0080906 A1 | 3/2015 | Fjorback et al. |
| 2015/0109006 A1 | 4/2015 | Choi et al. |
| 2015/0164552 A1 | 6/2015 | Chen et al. |
| 2015/0177079 A1 | 6/2015 | Eichhorn et al. |
| 2015/0216644 A1 | 8/2015 | Cahill et al. |
| 2015/0273236 A1 | 10/2015 | Rogers |
| 2015/0377815 A1 | 12/2015 | Wiklof et al. |

(56) References Cited

U.S. PATENT DOCUMENTS

FOREIGN PATENT DOCUMENTS

| WO | WO2011041507 A1 | 4/2011 |
| WO | WO2011079390 A1 | 7/2011 |
| WO | WO2014003878 A1 | 1/2014 |

OTHER PUBLICATIONS

"A carbon nanotubelpolymer strain sensor with linear and anti-symmetric piezoresistivity," Gang Yin et al. Published online before print Apr. 26, 2011. doi:10.1177/0021998310393296 Journal of Composite materials, Jun. 2011 vol. 45, No. 12 1315-1323.

"Flexible Strain Sensor Based on Carbon Nanotube Rubber Composites", Jin-Ho Kim et al., Nanosensors, Biosensors and Info-Tech Sensors and Systems 2010, edited by Vijay K. Varadan, Proc. of SPIE vol. 7646, 7646ON.

"Piezoresitive response of epoxy composites with carbon nanoparticles under tenssile load", Wichmann, Malte H.G., et al., Physical Review b80, 245437 (2009, The American Physical Society).

"Supersensitive linear piezoresistive property in carbon nanotubeslsilicone rubber nanocomposites," Zhi-Min Dang et al., Journal of Applied Physics, 104, 024114 (2008), American Institute of Physics.

Bozovic, et al., Plastic Deformations in Mechanically Strained Single-Walled Carbon Nanotubes, Department of Physics and Chemistry and Chemical Biology. Harvard University MA02138 (16 pages).

Wichmann et al., Phys. Rev. B 80, 245437, 2009.

Tekscan Inc., Integrating Force Sensors into Robotic Surgery, Medical Design Briefs 2013 (medicaldesignbriefs.com), 1 page. Tekscan, Inc. South Boston, MA.

Application and File History for U.S. Appl. No. 13/397,737, filed Feb. 16, 2012, inventors Eichhorn et al.

Application and File History for U.S. Appl. No. 13/599,935, filed Aug. 30, 2012, inventors Eichhorn et al.

Application and File History for U.S. Appl. No. 14/494,577, filed Sep. 23, 2014, inventors Eichhorn et al.

Application and File History for U.S. Appl. No. 14/137,984, filed Dec. 20, 2013, inventors Eichhorn et al.

Application and File History for U.S. Appl. No. 14/015,951, filed Aug. 30, 2013, inventors Eichhorn et al.

Application and File History for U.S. Appl. No. 14/208,575, filed Mar. 13, 2014, inventors Little et al.

Application and File History for U.S. Appl. No. 14/015,935, filed Aug. 30, 2013, inventors Eichhorn et al.

Application and File History for U.S. Patent Application No. PCT/US13/37731 filed Apr. 23, 2013, inventors Hilfiker et al.

Office Action, for U.S. Appl. No. 14/494,577, dated Jan. 4, 2017, 66 pages.

\* cited by examiner

Carbon Nanotube LIM Silicone Physical Properties
0.5%, 1%, 2% Loading of Multiwall Carbon Nanotubes

| Parameter | Plain LIM | 0.5% of CNT | 1% of CNT | 2% of CNT |
|---|---|---|---|---|
| Max. Torque, lb-in | 5.73 | 6.01 | 6.61 | 9.14 |
| TC90, Sec | 0.17 | 0.13 | 0.20 | 0.15 |
| Hardness, Shore A | 38 | 40 | 43 | 43 |
| Tensile, psi | 365 | 335 | 392 | 449 |
| Elongation, % | 256 | 227 | 230 | 265 |
| Modulus, psi | 168 | 160 | 197 | 220 |
| Tear, ppi | 30.4 | 28.6 | 41 | 52 |
| Sp.Gr | 1.255 | 1.31 | 1.31 | 1.284 |
| Compression set, % 22 hrs @ 350°f | 2.0 | 3.2 | 7.0 | 12.5 |
| Volume change in silicone oil,% 22hrs @ 350°F | 34 | 43 | 35 | 35 |
| Electrical resistivity, Ohm.cm | 10^13 | 5x10^4 | 1.3x10^3 | Out of range, too low |
| | | | | |

Fig. 1

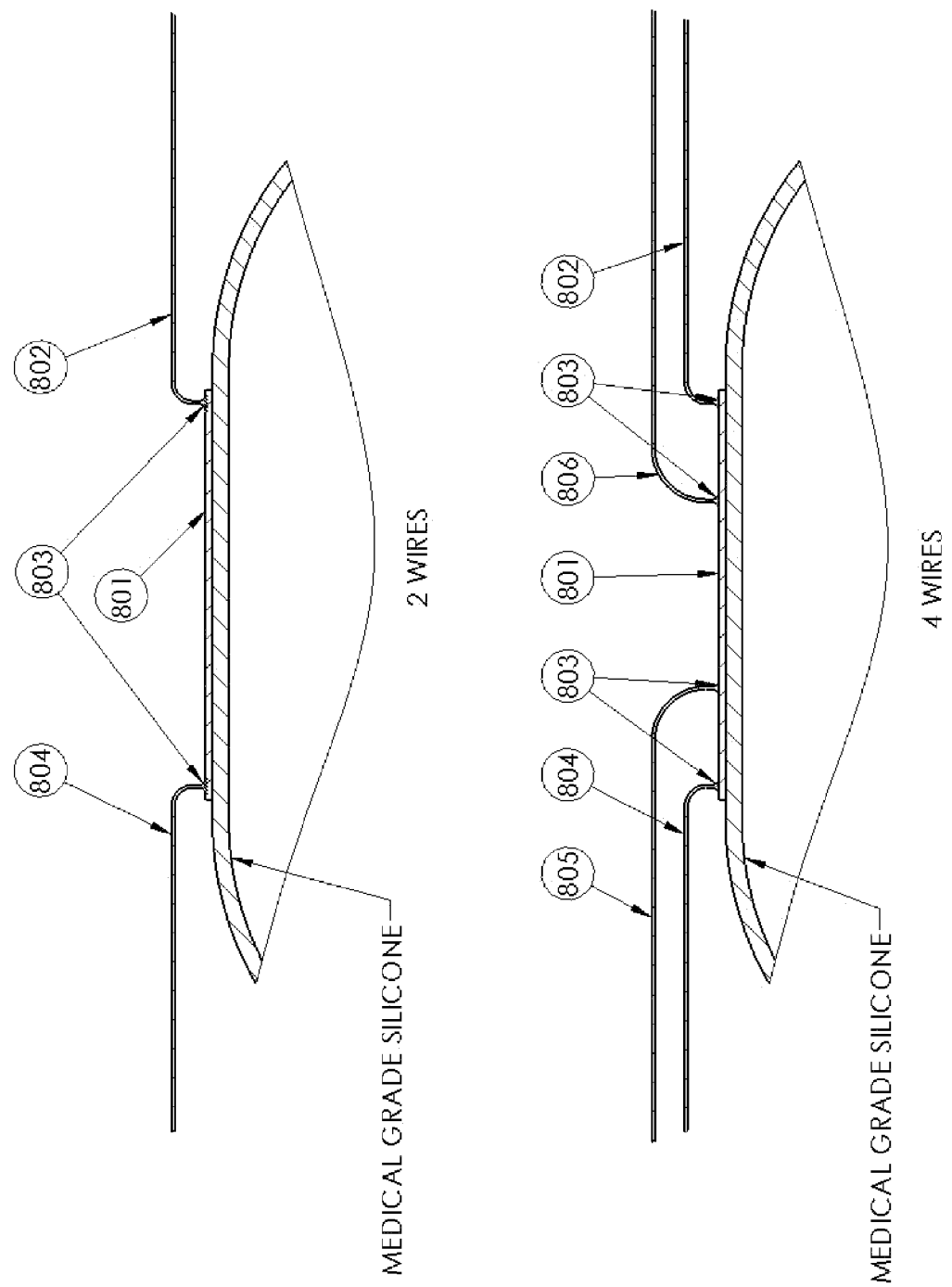

FLEXIBLE ELECTRICALLY CONDUCTIVE NANOTUBE SENSOR FOR ELASTOMERIC DEVICES

RELATED APPLICATIONS DATA

This application is a Continuation of U.S. patent application Ser. No. 13/399,935, filed Aug. 30, 2012, which is in turn a Continuation-in-Part application of and claim priority under 35 USC 120 from U.S. patent application Ser. No. 13/397,737 filed Feb. 16, 2012.

BACKGROUND OF THE INVENTION

1. Field of Invention

The present invention relates to the field of sensors, particularly sensors that indicate local changes in conditions in or on articles, and more particularly in the field of positionable sensors that can be applied to a surface, embedded in or constructed within a device which expands or flexes under pressure. The invention also relates to flexible electrical sensors for use in various technologies including at lest medical applications to provide information or measurement on the stress, elongation, pressure, or load that is applied to or placed upon the sensor. The present invention may be used as part of a device or system to provide information or measurement of stress, elongation, pressure, or load in the expansion of the device even in medical fields. In particular, the flexible nanotube composite sensor is bonded to or molded within an expandable and/or flexible elastomeric medical device system, such as a balloon (such as those delivered through catheters), to measure the performance of the device.

SUMMARY OF THE INVENTION

A flexible element (e.g., film, coating, patch or strip) of elastomeric polymer containing from 0.02 to 8% by total weight of conductive nanotubes provides a useful piezoresistive sensor. These sensors are attached to surfaces of or molded within the expandable or flexible elastomeric device, and measurements may be taken of changes in resistivity through or across the device (e.g., by measuring low voltage current across the strip) to determine changes in dimensions, stress and pressure on the strip. By having secure attachment to the surface of the expandable device or having it molded within the expandable device, changes in the dimensions, pressure and stress on the device may be estimated with a significant degree of assurance of meaningful results.

BRIEF DESCRIPTION OF THE FIGURES

FIG. 1 is a table showing a graphic representation of date relating physical properties of carbon nanotube silicone rubber composites within the generic scope of the present invention.

FIG. 6 is a side sectional view of an electrically conductive polymer sensor 1 comprising of nanotubes to confer electrical properties.

FIG. 8 shows an example of embodiment of a sensor on a surface of an inflatable balloon element within the generic scope of the present invention.

DETAILED DESCRIPTION OF THE INVENTION

Figure 2:
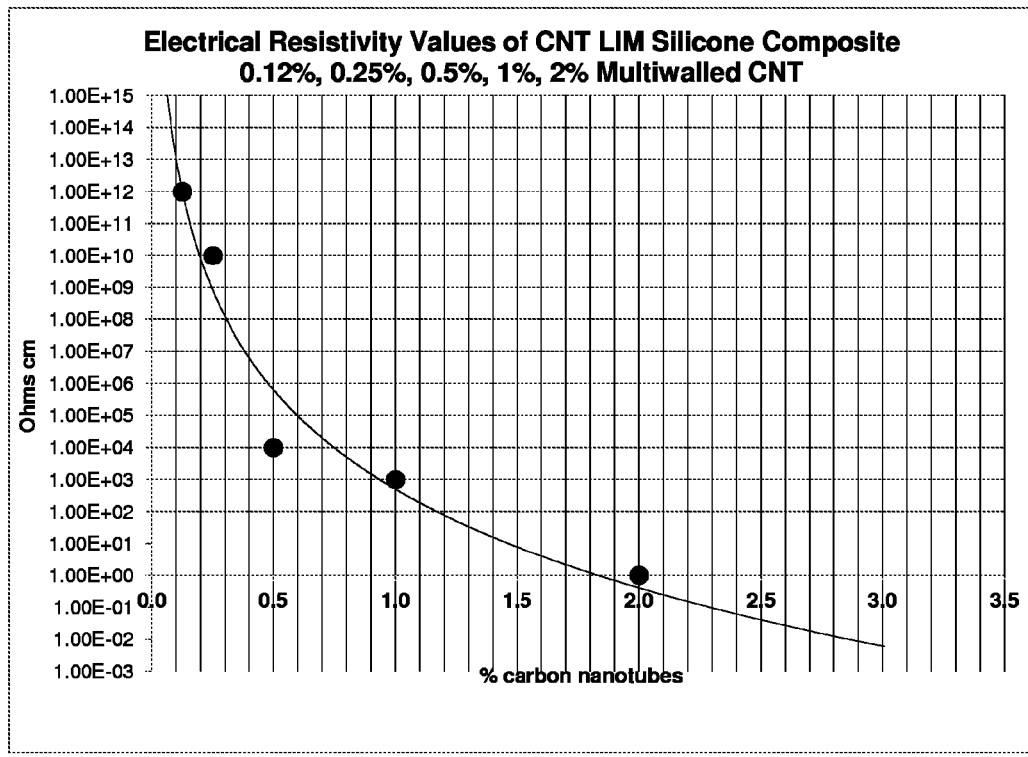
FIG. 2 is a graphic representation showing electrical resistivity properties of several carbon nanotube silicone rubber composites.

The following definitions and descriptions are useful in understanding the scope of technology used in the practice of the present technology.

Nanocomposite Definition:

Nanomaterials that combine one or more separate components in order to obtain the best properties of each component (composite). In nanocomposite, nanoparticles (clay, metal, carbon nanotubes) act as fillers in a matrix, usually polymer matrix.

Nanomaterials Definition:

nanomaterials can be defined as materials which have structured components with at least one dimension less than 100 nm. Materials that have one dimension in the nanoscale are layers, such as a thin films or surface coatings. Some of the features on computer chips come in this category. Materials that are nanoscale in two dimensions include nanowires and nanotubes. Materials that are nanoscale in three dimensions are particles, for example precipitates, colloids and quantum dots (tiny particles of semiconductor materials). Nanocrystalline materials, made up of nanometer-sized grains, also fall into this category. Preferred dimensions for nanotubes are diameters of from 3 Angstroms, preferably at least 5 Angstroms, more preferably at least 10 Angstroms up to 100 nm, preferably up to 70 nm, more preferably up to 50 nm. Preferred ranges of diameters for nanotubes according to the present invention are from 0.5 nm to 30 nm.

Nanometer Definition:

One nanometer (nm) is equal to one-billionth of a meter, $10^{-9}$ m. Atoms are below a nanometer in size, whereas many molecules, including some proteins, range from a nanometer upwards.

Nanoparticle Definition:

Nanoparticles are particles of less than 100 nm in diameter. The preferred size range for diameters of nanotubes described above tends to be a preferred range for the largest dimension of nanoparticles also.

Nanotube Definition (Carbon Nanotubes):

Carbon nanotubes (CNTs) were discovered by Sumio Iijima in 1991. Carbon nanotubes are generally fullerene-related structures which consist of rolled graphene sheets, although multiple molecular level structures of nanotubes and variations in structure have been created and described. There are two generic types of CNT: single-walled (one tube) or multi-walled (more tubes). Both of these are typically a few nanometers in diameter and several micrometers to centimeters long.

Nanowires Definition:

Nanowires are ultrafine wires or linear arrays of dots, made from a wide range of materials, with nanodimension diameters. These are essentially extremely long nanotubes in some instances.

Elastomeric Polymers

Elastomers are usually thermoset resins (requiring cross-linking or vulcanization) but may also be thermoplastic polymers. The polymer chains are cross-linked during curing, i.e., vulcanizing. The molecular structure of elastomers can be imagined as a 'spaghetti and meatball' structure, with the meatballs signifying cross-links. The elasticity is derived from the ability of the long chains to reconfigure themselves to distribute an applied stress. The covalent cross-linkages ensure that the elastomer will return to its original configuration when the stress is removed. As a result of this extreme flexibility, elastomers can reversibly extend (at least once, and preferably repeatedly without inelastic deformation occurring) from 5-700%, depending on the specific material. Without the cross-linkages or with short, uneasily reconfigured chains, the applied stress would more likely result in a permanent deformation. Temperature effects are also present in the demonstrated elasticity of a polymer. Elastomers that have cooled to a glassy or crystalline phase will have less mobile chains, and consequentially less elasticity, than those manipulated at temperatures higher than the glass transition temperature of the polymer. It is also possible for a polymer to exhibit elasticity that is not due to covalent cross-links. For example, crystalline polymers can be treated to alter their short range versus long range crystalline morphology to alter the elastic properties as well as other physical properties.

Underlying technology within the scope of the present invention includes both sensors and methods of using sensors in processes or procedures. The novel articles used as sensors in the practice of the present technology comprise millimeter dimension (diameters and or three major dimensions between 0.2 to 100 mm) polymeric structures comprising from 0.2% to 8% by total weight of conductive nanotubes. The articles must have some degree of elastic deformation properties. For example, the article should be able to deform (bend, stretch, flex, extend, etc.) such that in at least one dimension (e.g., the length of a nanotube) there can be at least 5% total elastic deformation. That deformation could be measured from a base line 0 stress article with a return to that base line 0 stress (unstressed) length that has not inelastically changed by more than 0.5%. When used, the articles must have electrodes attached across the conductive dimension of the article, preferably aligned with the dimension of expected stress and elongation. Although the electrodes may be separated so as to extend perpendicularly or acutely or obtusely with respect to the expected dimension of elongation and stress, the peizoresistive effect is more accurately measured along a single dimension (or possibly along multiple directions, as the nanotubes often are not uniformly aligned, but may curl and twist into three dimensional form) parallel with the stress and elongation. The article may have electrodes fixed into the structure or may have attachment points for attaching the electrodes and placing them into contact with the conductive layer. The electrodes would extend to and be in electrical communication connection with a current or voltage measuring system. A voltage is applied across the conductive layer (the polymer-containing nanotubes) in the sensor, which may again be parallel with, perpendicular to or angled with respect to at least one dimension along which stress and elongation is expected during use, and the changes in the current (and/or voltage) is measured and the changes are correlated to stress and/or percentages of elongation in the article. As the current passed between sensors will change in a repeatable manner no matter what the orientation between the current flow and the elongation/pressure may be, a look-up table or other correspondence between the elongation/strain/pressure and changes in current can be established as a reference.

The flexible, elastic and/or expandable article, such as a strip or patch, may be secured to a surface or molded within an expandable elastomeric device that is to be manipulated or mechanically processed or chemically processed, where such processing or handling has surrounding concerns about changes in stress, dimensions, pressure or the like that can be measured by piezoresistive measurements. An elongate element, such as a sensor tube for example, may be a conductive nanotube-containing polymer of from 0.2 to 10 mm in diameter, and from 2 to 100 mm in length. A patch may comprise a square or rectangular OR oval or other geometric shape flat material comprising a conductive nanotube-containing polymer and two opposed edges. The electrodes are positioned at or about the opposed edges, the current is passed through the polymer, stress is applied to the patch, and the change in current is measured and correlated with amounts of stress and/or dimensional changes.

Various aspects of the invention include a piezoresistive sensor having an electrically conductive elastic body having at least one pair of opposed ends, and the elastic body containing conductive nanotubes homogeneously distributed therein, the elastic body having at least one surface with physical attaching elements thereon and the elastic body having electrodes attached at each of the at opposed ends. The conductive elastic body (that is the actual body of the sensor made from a composition) has an elastic range of between about 5% elongation and about 500% elongation. The conductive elastic body may have for example, from about 0.02% to 8% by total weight of the elastic body (not including electrodes) of conductive nanotubes. Preferably the conductive nanotubes are from about 0.2 to 5% by total weight of the conductive elastic body. The conductive nanotubes may be carbon nanotubes. The elastic body may be a polymer as described herein. The polymer may, by way of non-limiting examples, be selected from the group consisting of epoxy resins, silicone resins, ethylenically unsaturated elastomeric resins, and natural rubbers. The physical attaching elements are selected from the group consisting of polymers, chemical adhesives, adhesive tapes or mechanical attachments.

The present technology also includes a method of sensing dimensional changes, stress changes or pressure changes on a substrate including steps (not necessarily in the following order) of: non-destructively attaching a piezoresistant sensor to a surface of the device or molding the piezoresistant sensor within the device, the piezoresistant sensor comprising an electrically conductive elastic body having at least one pair of opposed ends, and the elastic body containing conductive nanotubes homogeneously distributed therein, the elastic body having at least one surface with two opposed ends and electrodes at each of the opposed ends, passing a current through the elastic body between the two electrodes, sensing the current passing through the elastic body, performing a mechanical step on the substrate, and measuring changes in the current between the electrodes. The measured changes are identified by an electronic look-up table or other execution of software by a processor receiving information/ signals of the changes to identify changes in properties or conditions that are being monitored. The information may then be displayed on a video monitor if desired. The measured changes in current between the electrodes is related by execution of code in a processor to a pressure, stress level or change in dimension during performing of the expansion of the device mechanical step.

The invention also relates to a flexible electrically sensor for use in any inflatable or flexible device on which stress or dimensional changes are to be determined, by way of non-limiting examples, tubes, balloons or coronary, vascular, orthopedic, and pelvic health applications and devices to provide information or measurement on the stress, elongation, pressure, or load that is applied to a expandable balloon medical device during, for example, a medical procedure or long term retention within the body.

The present invention may be described as a flexible substrate having a major surface and a sensor attached to and aligned with the major surface of the substrate, wherein:

the sensor comprises an elastic body containing conductive nanotubes homogeneously distributed therein to form a conductive path and two electrodes in electrical connection with the conductive path. At least two electrodes of the sensor may be in communication with both a power source and a processor. The sensor may be adhered to the major surface or embedded in the major surface. The major surface is preferably non-conductive. The major surface may comprise an elastomeric composition having a first modulus of elasticity and the elastic body of the sensor has a second modulus of elasticity and wherein the first modulus of elasticity is within 40% of the second modulus of elasticity. The major surface may be on an inflatable balloon having a conduit for transporting fluid into a cavity of the balloon to alter stress on the major surface of the inflatable balloon. The substrate may operate wherein presence of a nominally maximum fluid volume within the cavity maintains at least a 0.01 mm/m extension of a dimension in the elastic body of the sensor. The substrate may have the two electrodes of the sensor in communication with both a power source and a processor. The sensor may comprise an elastic body of a silicone rubber containing a loading of between 0.5% and 3%, by total weight of conductive nanotubes. The substrate may have the major surface as part of an inflatable balloon having a conduit for transporting fluid into a cavity of the balloon to alter stress on the major surface of the inflatable balloon. The substrate may be part of the major surface which is in turn an elastomeric composition having a first modulus of elasticity and the elastic body of the sensor has a second modulus of elasticity and wherein the first modulus of elasticity is within 40% or within 35% or preferably within 25% of the second modulus of elasticity. The major surface may be on an inflatable balloon having a conduit for transporting fluid into a cavity of the balloon to alter stress on the major surface of the inflatable balloon. The major surface may be on an expandable balloon element in a medical device that applies localized pressure in a patient. The sensor may comprise an electrically conductive silicone rubber composite comprised of a liquid silicone rubber with a multi-wall carbon nanotube loading of between 1%-3% by weight and a hardness between 10 and 60 Asker C hardness.

The invention may also include a method of detecting stress, pressure or dimensional changes within an environment comprising positioning within the environment a substrate having a major surface and a sensor attached to and aligned with the major surface of the substrate, the sensor comprises an elastic body containing conductive nanotubes homogeneously distributed therein to form a conductive path and at least two electrodes in electrical connection with the conductive path;

applying a current across the sensor through one of the at least two electrodes;

determining changes in the current; and providing signals indicating changes in the current to a processor; and the processor executing code to correlate determined changes in the current to stress, pressure or dimensional changes in the sensor. These methods may use the substrates, sensors, devices and compositions described herein.

The composition of the balloon may be biocompatible or non-biocompatible elastomeric material. Exemplary of the biocompatible polymer material used in forming the balloons, the links or the stress concentrators includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), polyether-ether-ketone (PEEK), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (HI) core, polymers augmented with protons (H+), butadiene and isoprene (Kraton) and polyester thermoplastic elastomer (Hytrel), polyethylene, PLA, PGA, and PLGA.

The balloons may be part of devices and treatments for many varieties of medical procedures in which balloons or any expandable device is used to create pressure, increase volume restrictions, deliver materials, remove materials, stabilize organs, and the like. Non-limiting examples of such procedures include at least treatment of vascular occlusions, gastric insertions, spinal stabilization, aneurism stabilization, drug delivery implants, joint stabilization, bone stabilization, organ stabilization, delivery of medical devices, infusion devices, penile implants, bladder control devices, intestinal controls, urethral implants, orthopedic implants and the like.

The following description of the Figures will further assist in an understanding of the present technology.

FIG. 1 is a table showing a graphic representation of date relating physical properties of carbon nanotube silicone rubber composites within the generic scope of the present invention. The table shows those properties of materials composed of a base-platinum-cured, liquid silicone composition curable to a rubber, the curable composition loaded with concentrations of 0.5%, 1% and 2% commercially available multi-wall carbon nanotubes.

FIG. 2 is a graphic representation showing electrical resistivity properties of several carbon nanotube silicone rubber composites. Loading of 0.12%, 0.25%, 0.5%, 1.0% and 2.0% of commercially available multi-wall carbon nanotubes was added to a standardized composition of platinum cured liquid silicone rubber given in FIG. 1. Unless stated otherwise, the standard elastomer used in all examples (for convenience and to allow facile comparison of results only, a single composition was used, although not limiting the scope of the invention and presented with all data provided herein) was Shin Etsu X-34-1372, a two part, platinum cured liquid silicone rubber. The nanotubes were multiwall carbon nanotubes manufactured by Hyperion Catalysis and are approximately 4 nm in diameter by 1 micron or less in length.

The resultant electrical resistivity values, measured in Ohms cm, are plotted. The dramatic drop in electrical resistivity with very low loadings of carbon nanotubes is evident. The present invention may incorporate compositions displaying the electrical resistivity properties shown in FIG. 2 for a nanotube sensor, or other compositions, as generically described herein that display sufficient levels of resistance and piezoelectric resistivity as described herein.

Figure 3:
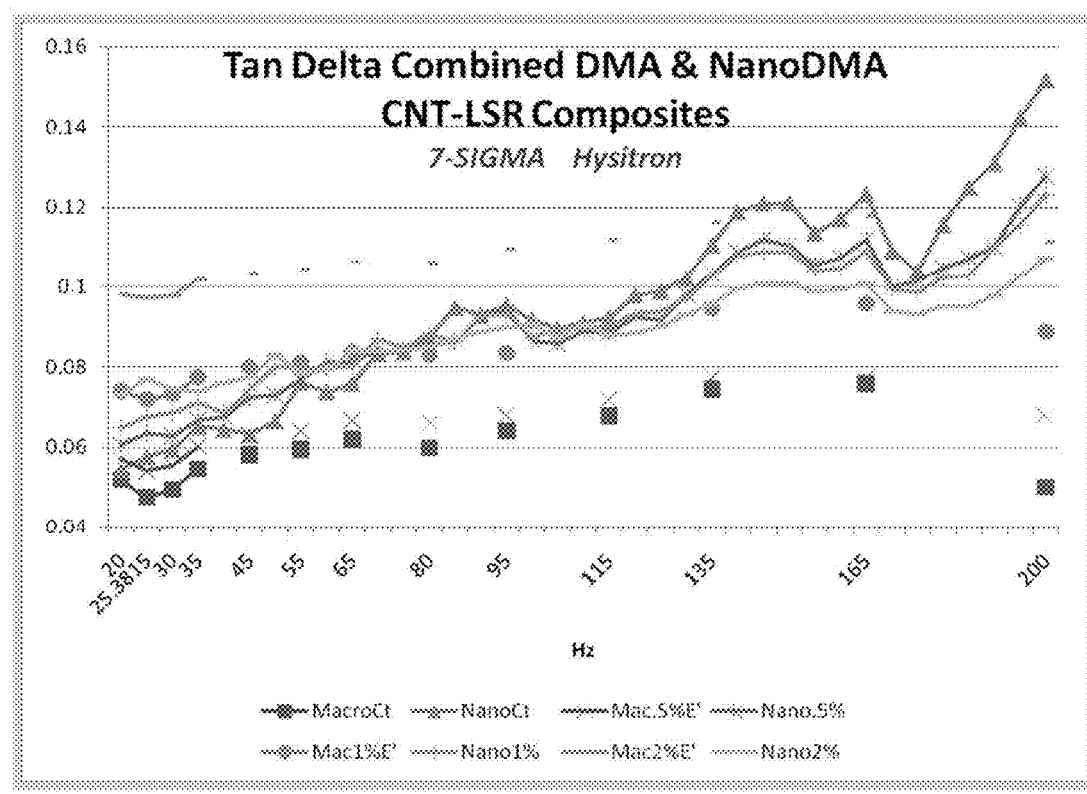
FIG. 3 is a graph showing the Dynamic Mechanical Analysis (DMA) Tan Delta (ratio between Storage and Loss Modulus) and nano-DMA testing of a carbon nanotube silicone rubber composite materials as presented in FIG. 1.

FIG. 3 is a graph showing the Dynamic Mechanical Analysis (DMA) Tan Delta (ratio between Storage and Loss Modulus) and nano-DMA testing of a carbon nanotube silicone rubber composite materials as presented in FIG. 1. The DMA plot is Tan Delta which is a ratio of the storage and loss modulus. Also are plotted a conventional DMA test with the nanoDMA testing. Dynamic Mechanical Analysis was carried out by Akron Research & Development Labs using a Visco Analyzer 2000 DMA150 in compression mode. Nanomechanical measurements were performed on a Hysitron TI 900 TriboIndenter™ tester by Hysitron, Inc. The graphically displayed results show the relationship between the DMA and the nano-DMA measurements of a frequency sweep from 20 to 200 hertz, and indicate a correlation of dynamic mechanical properties at the micro and nano levels of performance under strain. The indications are that the low loadings of carbon nanotubes within the general scope of the present invention (e.g., 0.5% to about 3% by total weight of the composition) does not adversely affect the mechanical performance of the material compared to the un-filled base material, thus preserving the physical properties of the chosen base polymer.

Figure 4:
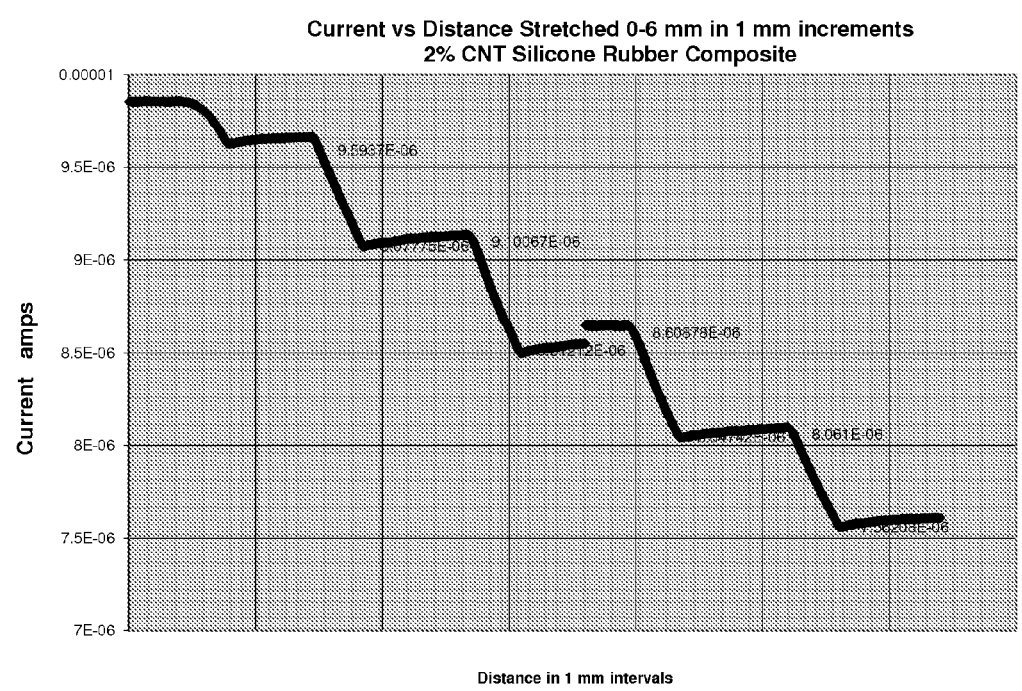
FIG. 4 graphically shows the piezoresitive response, measured by the change in current, of a flexible nanotube sensor as the flexible elastomeric device is inflated, in which the carbon nanotube sensor is molded.

FIG. 4 shows the piezoresitive response, measured by the change in current, of a flexible nanotube sensor, composed of material chosen from, but not limited to, FIG. 2, as it is stretched as the flexible elastomeric device is inflated, in which the cnt sensor is molded.

Figure 5:
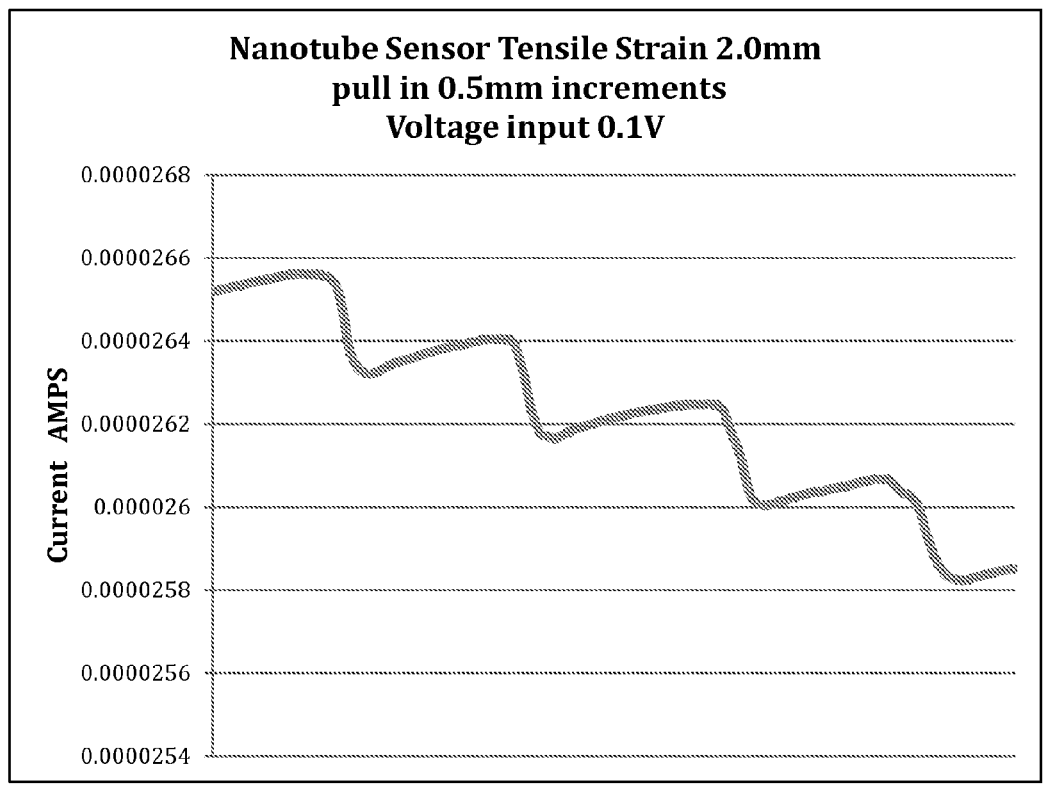
FIG. 5 graphically shows the piezoresitive response, measured by the change in current, of the nanotube sensor as it expands along with the flexible elastomeric device and places pressure, up to 10 Newtons, on a very soft rubber material.

FIG. 5 shows the piezoresitive response, measured by the change in current, of the nanotube sensor, composed of material chosen from, but not limited to, FIG. 2 as it expands along with the flexible elastomeric device and places pressure, up to 10 Newtons, on a very soft rubber material.

Figure 6:
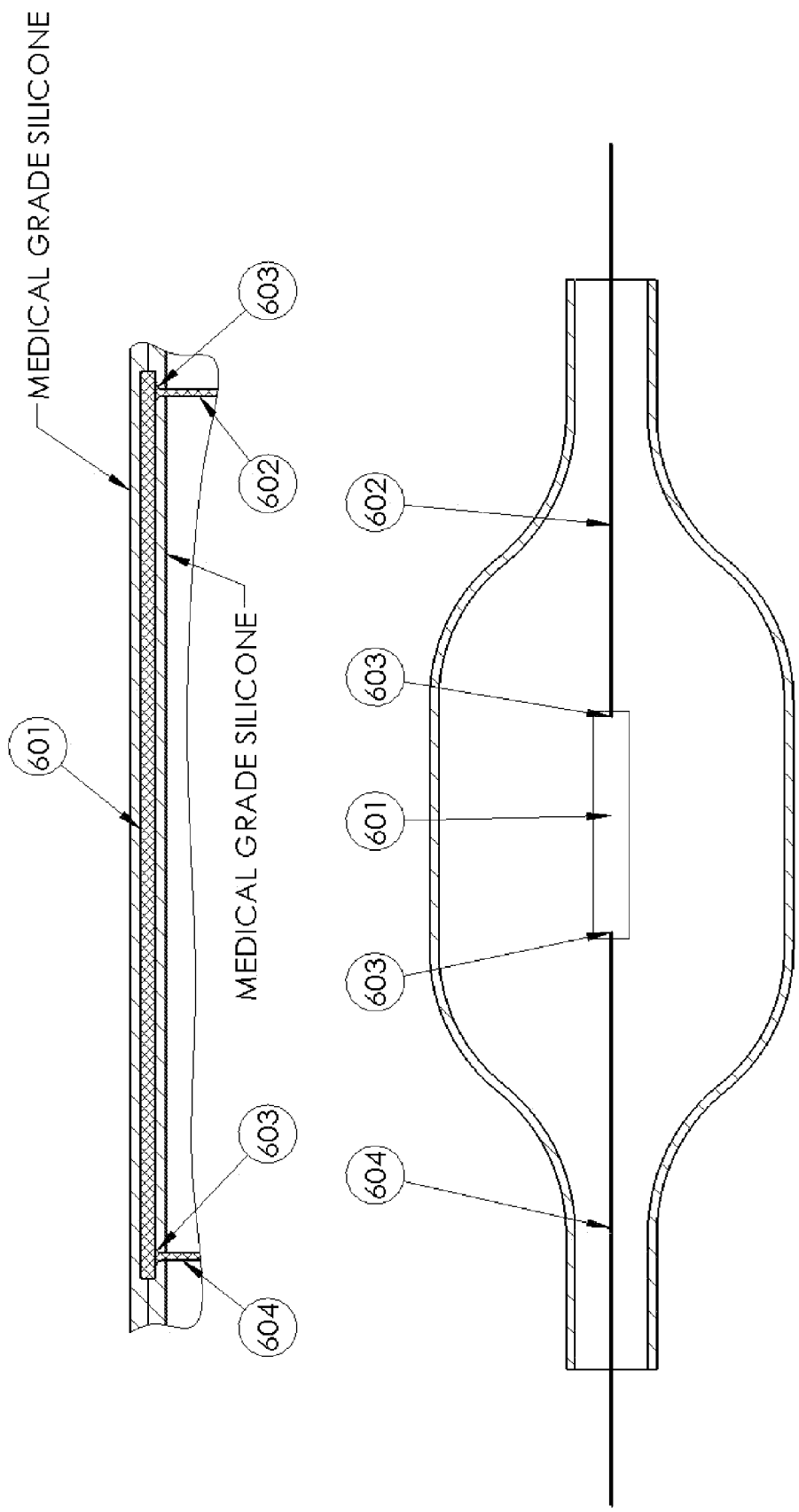
FIG. 6 shows an example of embodiment of a sensor within the generic scope of the present invention.

FIG. 6 shows an example of embodiment of a sensor within the generic scope of the present invention. FIG. 6 is a side sectional view of an electrically conductive polymer sensor 1 comprising of nanotubes to confer electrical properties. The sensor is comprised of the cured silicone polymer (or equivalent elastomer or flexible polymer). This is a flexible silicone rubber with carbon nanotube uniformly (essentially homogeneously, within the limits of real physical limits on the use of finite material) dispersed within the polymer at a preferred loading of between 0.5% and 3.0%. On each end of material 1 an electrical wire 2 and 4 (electrode) and connection 3 which are molded or affixed to the carbon nanotube rubber 1. The sensor is molded within the elastomeric medical balloon device, where a medical grade polymer encompasses the sensor. The sensor 601 is shown with its two leads 602 604 attached at points 603 embedded within medical grade silicone layers. A second embodiment is shown with the sensor 601, leads 602 604 and connection points 603 carried within the volume of an inflated balloon.

Figure 7:
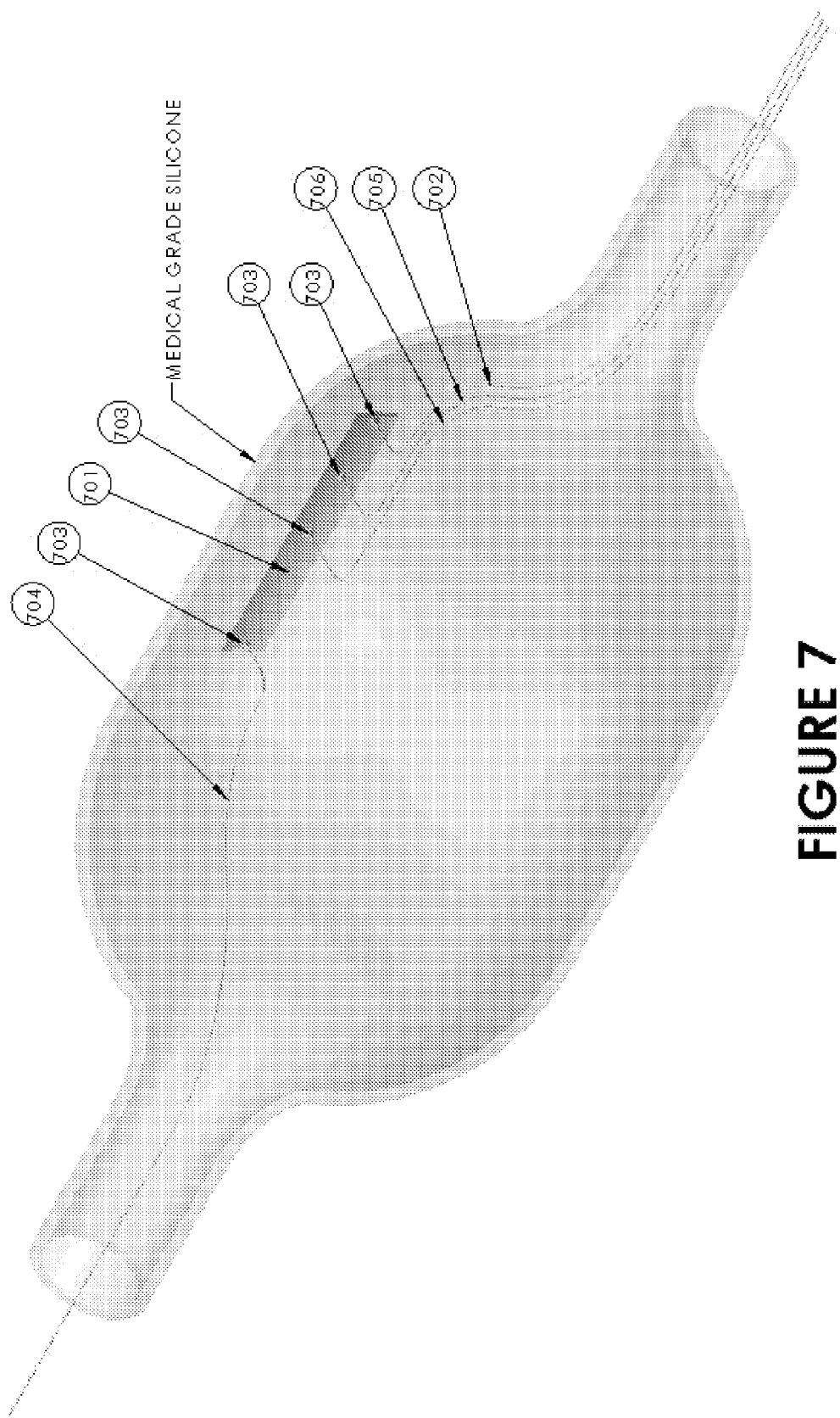
FIG. 7 shows an example of embodiment of a sensor on a surface of an inflatable balloon element within the generic scope of the present invention.

FIG. 7 shows an example of embodiment of a sensor within the generic scope of the present invention. FIG. 7 is a side sectional view of an electrically conductive polymer sensor 1 comprising of nanotubes to confer electrical properties. The sensor is comprised of the cured silicone polymer (or equivalent elastomer or flexible polymer). This is a flexible silicone rubber with carbon nanotube uniformly (essentially homogeneously, within the limits of real physical limits on the use of finite material) dispersed within the polymer at a preferred loading of between 0.5% and 3.0%. On each end of material 701 an electrical wire 702 and 704 (electrode) and connection 703 which are molded or affixed to the carbon nanotube rubber 701. Additionally, for example, between electrical wires 702 and 704 additional wires 705 and 706 may be applied, and connection 703 the sensor is molded within the elastomeric medical balloon device, where a medical grade polymer encompasses the sensor. The total number of wires connected to conductive polymer 701 may be 3 or more. The sensor is molded within the elastomeric medical balloon device, where a medical grade polymer encompasses the sensor.

FIG. 8 shows examples of embodiment of a sensor within the generic scope of the present invention. FIG. 8 is a side sectional view of an electrically conductive polymer sensor 1 comprising of nanotubes to confer electrical properties. The sensor is comprised of the cured silicone polymer (or equivalent elastomer or flexible polymer). This is a flexible silicone rubber with carbon nanotube uniformly (essentially homogeneously, within the limits of real physical limits on the use of finite material) dispersed within the polymer at a preferred loading of between 0.5% and 3.0%. On each end of material 801 an electrical wire 2 and 4 (electrode) and connection 803 which are molded or affixed to the carbon nanotube rubber 801. Additionally, for example, between electrical wires 802 and 804 additional wires 805 and 806 may be applied, and connection 3 the sensor is molded within the elastomeric medical balloon device, where a medical grade polymer encompasses the sensor. The total number of wires connected to conductive polymer 801 may be 3 or more. The sensor is affixed to a surface, interior or exterior, of the elastomeric medical balloon device.

To achieve desired or designed electrical properties to a polymer or elastomer as described herein, such as an epoxy resin, elastomeric polymer or rubber, addition of moderate percentages, such as between 0.5% up to 4% by total weight of the polymer of conductive nanoparticles and especially carbon nanoparticles may be used. Loading with larger conductive particles such as carbon black at levels above 10% by total weight of the composition or total weight of the elastomer, often result in compromised physical properties such as hardness, tensile, thermal and compression. In addition, the electrical conductivity is negatively altered upon large deformations of the material to the point whereby electrical contact between the conducting particles is broken. The addition of very small amounts, even less than 2% by total weight of the composition (as described herein), of carbon nanotubes increases the electrical conductivity of the base material while preserving desired physical properties of the original polymer. The relatively lower loading of carbon nanotubes to a silicone rubber elastomer preserve desired original liquid silicone rubber physical properties such as hardness, tensile, elongation and compression. Low loading, by weight, of carbon nanotubes to a base polymer significantly changes the electrical properties. For example, a 0.5% or 1.0% loading of multi-wall carbon nanotubes dispersed into a liquid polymerizable to a silicone rubber, changes the resistivity of the original silicone rubber elastomer from $10^{13}$ Ωcm to $10^3$ Ωcm, with no significant change in the other important properties of the original properties. Additionally, large deformations of the nanotube composite do not negatively affect the electrical conductance of the material rather the electrical conductivity is maintained.

Also considered within the scope of this disclosure are: types of sensor devices and/or systems used to determine and/or measure strain or pressure. The sensors are used to determine and/or measure the amount of pressure or strain applied to an associated surface and used to determine and/or measure tissue thickness, and to determine or measure pressure and/or to provide pressure or strain data to a processor which correlates the pressure data with tissue thickness using a look-up table or other data structure. By knowing the strain or pressure data, a surgeon or technician can then determine the proper alignment of the device before completing the medical procedure.

The processor may be housed in a remotely programmable apparatus which also includes a memory for storing the script programs and the responses to voltage data flow. The remotely programmable apparatus may further include a microprocessor connected to the wires (effectively the communication device from the sensor, with or without a preamplifier), a user interface, and the memory. The microprocessor executes the script programs to identify the strain, communicate the results sets to the practitioner (e.g., through a monitor or printed output or audio signal), receive possible responses to the results of the data (e.g., a signal to readjust the device or reduce the exhibited strain), and transmit the responses to the server and/or monitor through communication networks.

The system may also include wireless communication between the voltage meter reading sensor output and the processor. For example, a microprocessor may be preferably connected to memory using a standard two-wire $I^2C$ interface or using a wireless connection. The microprocessor is also connected to user input buttons to initiate activity, alter read-outs requested, respond to signals from the sensor, start a print-out, and the like (as through an I/O port or dedicated printer port, LED, a clock and a display driver. The clock could indicate the current date and time to the microprocessor and measure duration of strain or pressure. The clock may be a separate component, but is preferably built into microprocessor. The display driver operates under the control of microprocessor to display information on a video display or monitor. The microprocessor may be any microprocessor in any format, including a laptop (PC or Mac) and operate on any operating system, including Linux. For example, a PIC 16C65 processor which includes a universal asynchronous receiver transmitter (UART) is an example of a useful processor for communicating with a modem and a device interface. A CMOS switch under the control of the microprocessor alternately connects modem and interface to the UART.

For the purposes of the implementation of the invention, a study was conducted using very low loadings of carbon nanotubes in an elastomeric liquid silicone rubber polymer. The resultant data concluded that desirable electrical properties were conferred to the liquid silicone rubber elastomeric polymer with relatively low, e.g., less than 4% or less than 3%, loadings of multi-walled carbon nanotubes. In addition, the study showed that the desired physical properties were maintained, and that no diluent behavior was observed. Further, the study showed that uniform resistivity was achieved throughout the liquid silicone carbon nanotube rubber composite. These conclusions support the inference that a liquid silicone carbon nanotube rubber composite can be effectively designed as an electrically conductive elastomeric material, while maintaining desirable physical properties such as tensile strength, elongation to break, compression and hardness.

Conventional and nano static and dynamic properties testing of materials, such as tensile, elongation, compression set, Dynamic Mechanical Analysis, surface and volume resistivity, etc., are often used to characterize material properties. Values from these tests are considered in the choice of materials suitable for application in the flexible sensor. Such test were conducted on carbon nanotube liquid silicone rubber composites to evaluate the effect of different loadings of carbon nanotube with different liquid rubbers. In addition for the purpose of the invention, a study was conducted using very low loading of carbon nanotubes in an elastomeric silicone rubber polymer, measuring the changes in the electrical resistivity of the composite polymer during deformation. The changes in resistivity were measured as a function in the change of the output current of the material with a constant voltage applied to the material. The study compared loadings, by weight, of carbon nanotubes homogeneously mixed in the standard silicone polymers of between 0.5% and 2%. The resultant composites were deformed under various loading conditions and the change in resistivity of the composite monitored. For the purpose of the medical application, the study used voltages of between 0.01 and 1 volts. The study conducted measured large repeated deformations such as tensile strain in the order of 10 mm elongation as well as small deformation in the order of microns. The resultant change in resistivity correlated with the amount of deformation or force applied to the polymer composite. Although the term "constant voltage" is used, other electrical measurements are also used. For example, a constant current may be used (and voltage measured) It is also possible to use any other means such as resistive bridge circuit configurations or ballast circuits to determine resistance change.

Another aspect of the present technology includes accurate measurement of the amount of deformation of, strain exhibited on, or pressure exerted upon, an elastomeric medical device or component or sub-component inserted into a patient is determined by utilizing a sensor as described herein attached to or molded within the elastomeric medical device and exhibiting the above described piezoresitive properties that conductive nanotubes confer to an elastic medium. Such a sensor can be used to measure elongation or strain of a medical device during insertion, or immediately after insertion or even long after insertion into the patient. Such a sensor can also measure the deformation or load that is placed upon the medical device by the organ or with the body part with which the medical device is in contact. That measurement may be a direct pressure measurement, or by comparing strain with known degrees of pressure applied perpendicular to the sensor (and using a look-up table). Such a sensor may also be used to measure the amount of pressure that is being applied to a body part by the medical device. Such a sensor may also be used to monitor changes over time of the elongation, deformation, strain, load or pressure of an object or body part to which the sensor is affixed.

The present invention also relates to an electrically conductive rubber whereby the conductive agent applied to a flexible polymer base may be carbon nanotubes. The carbon nanotubes loadings are dispersed homogeneously into the polymer base such that the flexibility of the original base polymer is not dramatically compromised, and such that the electrical response of the composite is not significantly compromised (e.g., by more than 15%) over repeated deformations (e.g., over 20 deformations with greater than 100% elongation). A constant voltage is applied to the sensor and the electrical current is monitored at a point some distance from the voltage input through electrical connection with the electrodes or wires on the sensor. As the sensor is deformed, the current will change in response to the deformation due to the change in electrical resistivity of the composite material. For sensing deformation in devices in medical applications, the input voltage may be very low, in the order of less than 1 volt (e.g., 0.05 up to 1 volt), depending upon the electrical conductivity of the composite polymer. For medical applications the nanotube composite may be incased within a flexible polymer to insulate the electrically conductive composite and to comply with FDA regulations that may concern nano particle exposure.

The invention further relates to a sensor for which elongation and/or stress of the sensor is directly related to the distance that the sensor, or the medical device to which the sensor is affixed, is pulled, stressed, flexed, expanded or compressed. The distance may be a continuous pull, inflated expansion or compression or an incremental pull, stress, inflated expansion or compression of the sensor. The change in resistivity of the nanotube composite sensor directly correlates to the change in distance that the sensor is pulled, stressed, flexed or compressed. The change in resistivity may be measured directly as a change in resistance or as the change in current when a constant voltage is applied. Additionally, the load placed upon the sensor, or the medical device to which it is affixed or molded within, can be determined likewise by the change in resistivity of the nanotube composite sensor.

Various other aspects of the invention also relate to a flexible electrically conductive nanotube silicone rubber composite that is contained within a non electrically conductive medical grade silicone rubber, for the express purpose of distance, inflated expansion, compression or load measurement by observing the change in electrically resistivity of the nanotube composite. The attaching element can be used to attach the sensor directly to other sensors or devices attached to a medical patient for the purpose of measuring the stress or strain or other applied forces to the device. Additionally a sensor is described having at least an elastic body containing conductive nanotubes homogeneously distributed therein, the sensor contained or attached to or molded within an elastic body not containing conductive nanotubes and not electrically conductive, of which at least one surface of the sensor with physical attaching element thereon. Where embedded in another material, the attaching members assure elongation along with the embedding body.

Another aspect of the technology includes a sensor comprising of an elastic body comprised of a silicone rubber containing a loading of between 0.5% and 3%, by wt. of conductive nanotubes such as carbon nanotubes, homogeneously distributed therein, with electrodes adhered to or molded within the nanotube composite for the purpose of applying an electrical current through the composite and a detection system that detects absolute amounts of voltage and/or changes in voltage across the electrodes.

A further aspect of the present technology may include a sensor having an elastic body comprised of a liquid silicone rubber containing a loading of between 0.5% and 3%, by wt. of carbon nanotubes, homogeneously distributed therein, with electrodes adhered to or molded within the nanotube composite and contained entirely within a medical grade non conductive flexible silicone rubber.

Another aspect of the present invention may include an electrically conductive silicone rubber composite comprised of a liquid silicone rubber with a multi-wall carbon nanotube loading of between 1%-3% by weight and a hardness between 10 and 60 Asker C hardness.

An electrically conductive silicone rubber composite comprised of a liquid silicone rubber with a multi-wall carbon nanotube loading of between 0.5%-3% by weight, a hardness of between 10 and 60 Asker C and elongation property greater than 200%.

An electrically conductive silicone rubber composite comprised of a liquid silicone rubber with a multi-wall carbon nanotube loading of between 1%-3% by weight, a hardness of between 10 and 60 Asker C, an elongation property greater than 200% and electrical resistivity of $10^3$ Ohm/sq or less.

Although specific dimensions, compositions, voltages, materials and fields of use are described herein, it must be understood that these are examples enabling the generic scope of the invention and should not limit the scope of enforcement of claims herein.

What is claimed:

1. An elastic piezoresistive sensor tube configured to sense a dimensional change during a medical procedure, the elastic piezoresistive sensor tube comprising:
   an elastic sensor tube body containing conductive nanotubes substantially homogeneously distributed within an interior of at least a portion of the elastic sensor tube body to form a conductive path, the elastic sensor tube body defining an internal conduit configured to transport fluid between a first end and a second end; and
   at least two electrodes in electrical connection with the conductive path;
   wherein the dimensional change is at least one of a stress in the elastic sensor tube body, a pressure applied to the elastic sensor tube body, an elongation of the elastic sensor tube body, and a load applied to the elastic sensor tube body.

2. The elastic piezoresistive sensor tube of claim 1, wherein the at least two electrodes are in communication with both a power source and a processor.

3. The elastic piezoresistive sensor tube of claim 1, wherein the elastic sensor tube body forms at least part of at least one of a medical device and a medical training device.

4. The elastic piezoresistive sensor tube of claim 1, wherein the elastic sensor tube body includes silicone rubber comprising a loading of between 0.5% and 3% by weight of conductive nanotubes.

5. The elastic piezoresistive sensor of claim 1, wherein the elastic sensor tube body comprises at least one of a conduit and a balloon.

6. The elastic piezoresistive sensor of claim 1, wherein the elastic sensor tube body is representative of human vasculature.

7. A method of detecting a dimensional change within an elastic tube used during a medical procedure, the method comprising:
   forming an elastic sensor tube body defining an internal conduit configured to transport fluid between a first end and a second end, the sensor tube body containing conductive nanotubes substantially homogeneously distributed within an interior of at least a portion of the elastic sensor tube body to form a conductive path between at least two electrodes;
   applying a current across the conductive path through the at least two electrodes;

providing signals indicating changes in the current to a processor, wherein the processor executes a code to correlate the determined changes in the current to at least one of a stress in the elastic sensor tube body, a pressure applied to the elastic sensor tube body, an elongation of the elastic sensor tube body, and a load applied to the elastic sensor tube body.

8. The method of claim 7 wherein, the elastic sensor tube body forms at least part of at least one of a medical device and medical training device.

9. The method of claim 7, wherein the elastic sensor tube body comprises at least one of a conduit and a balloon.

10. The method of claim 7, wherein the elastic sensor tube body is representative of human vasculature.

11. A sensor, comprising:
an elastic sensor tube body, comprising a non-conductive polymer defining an internal conduit configured to transport fluid between a first end and a second end, at least an interior portion of the elastic sensor tube body having a plurality of carbon nanotubes dispersed therein to form a conductive path; and
at least two electrodes, operably coupled to the elastic sensor tube body and in electrical communication with the conductive path;
wherein the sensor is configured to sense at least one of stress in the elastic sensor tube body, pressure applied to the elastic sensor tube body, an elongation of the elastic sensor tube body, and a load applied to the elastic sensor tube body.

12. The sensor of claim 11, wherein the elastic sensor tube body contains 0.5 to 3% by total weight of carbon nanotubes.

13. The sensor of claim 11, wherein the carbon nanotubes dispersed within the elastic sensor tube body are not uniformly aligned within the elastic sensor tube body.

14. The sensor of claim 11, wherein the elastic sensor tube body has an elastic range between about 5% elongation and about 500% elongation.

15. The sensor of claim 11, wherein the conductive path has an electrical resistivity of 103 Ohm/sq or less.

16. The sensor of claim 11, wherein the elastic sensor tube body has a hardness of between 10 and 60 Asker C.

17. The sensor of claim 11, wherein the non-conductive polymer is at least one of a silicone, an ethylenic elastomer, and a rubber.

18. The sensor of claim 11, further comprising a shell of non-conductive flexible material, the shell encasing the elastic sensor tube body and configured to electrically insulate the carbon nanotubes dispersed within the elastic sensor tube body from the surrounding environment.

19. The sensor of claim 11, wherein the carbon nanotubes are substantially homogeneously dispersed in the non-conductive polymer.

20. The sensor of claim 11, wherein the elastic sensor tube body comprises at least one of a conduit and a balloon.

21. The sensor of claim 11, wherein the elastic sensor tube body is representative of human vasculature.

* * * * *